United States Patent [19]
Bryan et al.

[11] Patent Number: 5,559,105
[45] Date of Patent: Sep. 24, 1996

[54] ENDOTHELIN RECEPTOR ANTAGONISTS

[75] Inventors: Deborah L. Bryan, West Chester; John D. Elliott, Wayne, both of Pa.

[73] Assignee: SmithKline Beecham Corporation, Philadelphia, Pa.

[21] Appl. No.: 374,544

[22] PCT Filed: Jul. 15, 1993

[86] PCT No.: PCT/US93/06667

§ 371 Date: Jan. 17, 1995

§ 102(e) Date: Jan. 17, 1995

[87] PCT Pub. No.: WO94/02474

PCT Pub. Date: Feb. 3, 1994

[51] Int. Cl.$^6$ ............... A61K 31/41; C07D 403/02
[52] U.S. Cl. ............... 514/63; 514/397; 514/399; 514/452; 514/464; 548/110; 548/311.7; 548/346.1; 549/434; 549/435; 549/445
[58] Field of Search ............... 548/346.1, 110, 548/311.7; 514/399, 63, 397, 464, 452; 549/434, 435, 445

[56] References Cited

U.S. PATENT DOCUMENTS

| | | | |
|---|---|---|---|
| 2,381,887 | 8/1945 | Sauer et al. | 260/410.8 |
| 4,760,174 | 7/1988 | Frickel et al. | 562/462 |
| 5,110,956 | 5/1992 | Ogata et al. | 549/447 |

FOREIGN PATENT DOCUMENTS

| | | |
|---|---|---|
| 0281098 | 9/1988 | European Pat. Off. |
| 0403158 | 12/1990 | European Pat. Off. |
| 57-212150 | 12/1982 | Japan |

OTHER PUBLICATIONS

CA103:101899a Antibacterial . . . β–aminoketones. Montginoul et al., p. 349, 1985.
CA118:38842u Antifungal agents. 1. Synthesis . . . derivatives. Massa et al., p. 678, 1993.
Buckley, et al., "Dependence of Aryl Ether Acylation upon Lewis Acid Stoichiometry", *Journal of the American Chemical Society* 102:9, pp. 3056–3062 (1980).

*Primary Examiner*—Joseph K. McKane
*Attorney, Agent, or Firm*—Linda E. Hall; Edward T. Lentz; Stephen A. Venetianer

[57] ABSTRACT

A compound of formula:

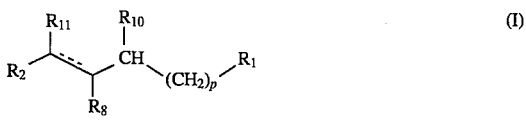

(I)

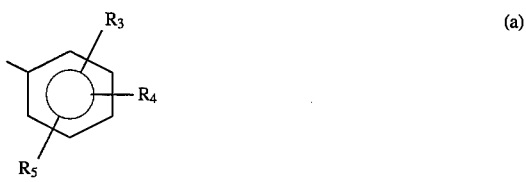

(a)

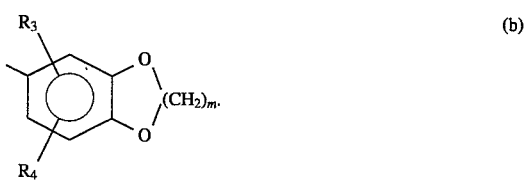

(b)

8 Claims, No Drawings

ENDOTHELIN RECEPTOR ANTAGONISTS

This application is a 371 of PCT/US93/06667 filed Jul. 15, 1993.

FIELD OF THE INVENTION

The present invention relates to novel compounds, pharmaceutical compositions containing these compounds and their use as endothelin receptor antagonists.

BACKGROUND

Endothelin (ET) is a highly potent vasoconstrictor peptide synthesized and released by the vascular endothelium. Endothelin exists as three isoforms, ET-1, ET-2 and ET-3. [Unless otherwise stated "endothelin" shall mean any or all of the isoforms of endothelin]. Endothelin has profound effects on the cardiovascular system, and in particular, the coronary, renal and cerebral circulation. Elevated or abnormal release of endothelin is associated with smooth muscle contraction which is involved in the pathogenesis of cardiovascular, cerebrovascular, respiratory and renal pathophysiology. Elevated levels of endothelin have been reported in plasma from patients with essential hypertension, acute myocardial infarction, subarachnoid hemorrhage, atherosclerosis, and patients with uraemia undergoing dialysis.

In vivo, endothelin has pronounced effects on blood pressure and cardiac output. An intravenous bolus injection of ET (0.1 to 3 nmol/kg) in rats causes a transient, dose-related depressor response (lasting 0.5 to 2 minutes) followed by a sustained, dose-dependent rise in arterial blood pressure which can remain elevated for 2 to 3 hours following dosing. Doses above 3 nmol/kg in a rat often prove fatal.

Endothelin appears to produce a preferential effect in the renal vascular bed. It produces a marked, long-lasting decrease in renal blood flow, accompanied by a significant decrease in GFR, urine volume, urinary sodium and potassium excretion. Endothelin produces a sustained antinatriuretic effect, despite significant elevations in atrial natriuretic peptide. Endothelin also stimulates plasma renin activity. These findings suggest that ET is involved in the regulation of renal function and is involved in a variety of renal disorders including acute renal failure, cyclosporine nephro-toxicity and chronic renal failure.

Studies have shown that in vivo, the cerebral vasculature is highly sensitive to both the vasodilator and vasoconstrictor effects of endothelin. Therefore, ET may be an important mediator of cerebral vasospasm, a frequent and often fatal consequence of subarachnoid hemorrhage.

ET also inhibits direct central nervous system effects such as severe apnea and ischemic lesions which suggests that ET may contribute to the development of cerebral infarcts and neuronal death.

ET has also been implicated in myocardial ischemia (Nichols et al. *Br. J. Pharm.* 99: 597–601, 1989 and Clozel and Clozel, *Circ. Res.*, 65: 1193–1200, 1989) coronary vasospasm (Fukuda et at., *Eur. J. Pharm.* 165: 301–304, 1989 and Lüscher, *Circ.* 83: 701, 1991) heart failure, proliferation of vascular smooth muscle cells, (Takagi, *Biochem & Biophys. Res. Commun.*; 168: 537–543, 1990, Bobek et al., *Am. J. Physiol.* 258:408–C415, 1990) and atherosclerosis, (Nakaki et al., *Biochem. & Biophys. Res. Commun.* 158: 880–881, 1989, and Lerman et al., *New Eng. J. of Med.* 325: 997–1001, 1991). Increased levels of endothelin have been shown after coronary balloon angioplasty (Kadel et al., No. 2491 *Circ.* 82: 627, 1990).

Further, endothelin has been found to be a potent constrictor of isolated mammalian airway tissue including human bronchus (Uchida et al., *Eur. J. of Pharm.* 154:227–228 1988, LaGente, *Clin. Exp. Allergy* 20: 343–348, 1990; and Springall et al., *Lancet,* 337: 697–701, 1991). Endothelin may play a role in the pathogenesis of interstitial pulmonary fibrosis and associated pulmonary hypertension, Glard et al., Third International Conference on Endothelin, 1993, p. 34 and ARDS (Adult Respiratory Distress Syndrome), Sanal et al., Supra, p. 112.

Endothelin has been associated with the induction of hemorrhagic and necrotic damage in the gastric mucosa (Whittle et al., *Br. J. Pharm.* 95:1011–1013, 1988); Raynaud's phenomenon, Cinniniello et al., *Lancet* 337:114–115, 1991); Crohn's Disease and ulcerative colitis, Munch et al., *Lancet, Vol.* 339, p. 381; Migraine (Edmeads, Headache, Feb. 1991 p 127); Sepsis (Weitzberg et al., *Circ. Shock* 33: 222–227, 1991; Pittet et al., *Ann. Surg.* 213: 262–264, 1991), Cyclosporin-induced renal failure or hypertension (*Eur. J. Pharmacol.*, 180:191–192, 1990, Kidney Int, 37:1487–1491, 1990) and endotoxin shock and other endotoxin induced diseases (Biochem. Biophys. Res. Commun., 161: 1220–1227, 1989, *Acta Physiol. Scand,* 137: 317–318, 1989) and inflammatory skin diseases. (*Clin Res.* 41:451 and 484, 1993).

Endothelin has also been implicated in preclampsia of pregnancy. Clark et al., *Am. J. Obstet. Gynecol.* March 1992, p. 962–968; Kamor et al,, *N. Eng. J. of Med.,* Nov. 22, 1990, p. 1486–1487; Dekker et al., *Eur J. Ob. and Gyn. and Rep. Bio.* 40 (1991) 215–220; Schiff et at., *Am. J. Ostet. Gynecol.* Feb 1992, p. 624–628; diabetes mellitus, Takahashi et al., *Diabetologia* (1990) 33:306–310; and acute vascular rejection following kidney transplant, Watschinger et al., *Transplantation* Vol. 52, No. 4, pp. 743–746.

Endothelin stimulates both bone resorption and anabolism and may have a role in the coupling of bone remodeling. Tatrai et al. *Endocrinology*, Vol. 131, p. 603–607.

Endothelin has been reported to stimulate the transport of sperm in the uterine cavity, Casey et al., *J. Clin. Endo and Metabolism,* Vol. 74, No. 1, p. 223–225, therefore endothelin antagonists may be useful as male contraceptives. Endothelin modulates the ovarian/menstrual cycle, Kenegsberg, *J. of Clin. Endo. and Met.,* Vol. 74, No. 1, p. 12, and may also play a role in the regulation of penile vascular tone in man, Lau et al., *Asia Pacific J. of Pharm.,* 1991, 6:287–292 and Tejada et al., *J. Amer. Physio. Soc.* 1991, H1078–H1085.

Thus, endothelin receptor antagonists would offer a unique approach toward the pharmacotherapy of hypertension, renal failure, cerebrovascular disease, myocardial ischemia, angina, heart failure, asthma, atherosclerosis, Raynaud's phenomenon, ulcers, sepsis, migraine, glaucoma, endotoxin shock, endotoxin induced multiple organ failure or disseminated intravascular coagulation, cyclosporin-induced renal failure and as an adjunct in angioplasty for prevention of restenosis, diabetes, preclampsia of pregnancy, bone remodeling, kidney transplant, male contraceptives, infertility and priaprism.

SUMMARY OF THE INVENTION

This invention comprises compounds represented by Formula (I) and pharmaceutical compositions containing these compounds, and their use as endothelin receptor antagonists which are useful in the treatment of a variety of cardiovascular and renal diseases including, but not limited to: hypertension, acute and chronic renal failure, cyclosporine induced nephrotoxicity, stroke, cerebrovascular vasospasm, myocardial ischemia, angina, hem failure, atherosclerosis, and as an adjunct in angioplasty for prevention of restenosis.

This invention further constitutes a method for antagonizing endothelin receptors in an animal, including humans, which comprises administering to an animal in need thereof an effective amount of a compound of Formula (I).

DETAILED DESCRIPTION OF THE INVENTION

The compounds of this invention are represented by structural Formula (I):

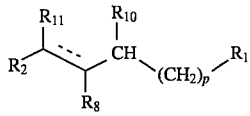

(I)

wherein:

$R_1$ and $R_2$ are independently:

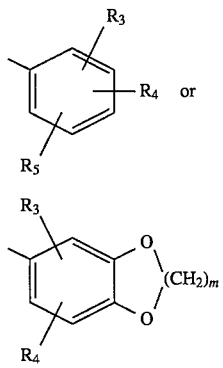

$R_3$ and $R_5$ are independently hydrogen, $R_{11}$, OH, $C_{1-8}$alkoxy, $-S(O)_p R_{11}$, $-N(R_6)_2$, Br, F, I, Cl, $CF_3$, $-NHCOR_6$, $-R_{11}CO_2R_7$, $-XR_9-Y$ or $-X(CH_2)_n R_8$ wherein each methylene group within $-X(CH_2)_n R_8$ may be unsubstituted or substituted by one or two $-(CH_2)_n Ar$ groups;

$R_4$ is hydrogen, $R_{11}$, OH, $C_{1-5}$alkoxy, $-S(O)_p R_{11}$, $-N(R_6)_2$, $-XR_{11}$, Br, F, I, Cl or $-NHCOR_6$ wherein the $C_{1-5}$alkoxy may be unsubstituted or substituted by OH, methoxy or halogen;

$R_6$ is independently hydrogen or $C_{1-5}$alkyl;

$R_7$ is independently hydrogen, $C_{1-10}$alkyl, $C_{2-10}$alkenyl or $C_{2-8}$alkynyl all of which may be unsubustituted or substituted by one or more OH, $N(R_6)_2$, $CO_2R_{12}$, halogen or $XC_{1-5}$alkyl; or $R_7$ is $(CH_2)_n Ar$;

$R_8$ is $R_{11}$, $-CO_2R_7$, $-CO_2C(R_7)_2O(CO)XR_{11}$, $-PO_3(R_7)_2$, $-SO_2NR_7R_{11}$, $-CONR_7SO_2R_{11}$, $-SO_3R_7$, $-SO_2R_7$, $-P(O)(OR_7)R_7$, CN, $-NR_7SO_2R_{11}$, $-C(O)N(R_6)_2$ or tetrazole;

$R_9$ is $(CH_2)_n$, $C_{1-10}$alkyl, $C_{2-10}$alkenyl or phenyl all of which may be unsubstituted or substituted by one or more OH, $N(R_6)_2$, COOH, halogen, >C=O or $XC_{1-5}$alkyl;

X is $(CH_2)_n$, O, $NR_6$ or $S(O)_p$;

Y is $CH_3$, $-X(CH_2)_n Ar$ or Ar;

$R_{10}$ is hydrogen, phenyl, benzyl, radical (b) from above, imidazolyl, thienyl, furyl, pyrazolyl, isoxazolyl, pyridyl or tetrazolyl all of which may be unsubstituted or substituted by $C_{1-6}$alkyl, $C_{1-6}$alkoxy, Cl, Br, F, I, $N(R_7)_2$, $-CO_2R_7$, $-SO_2NHR_7$, $-SO_3R_7$, $-CON(R_7)_2$, OH, $NO_2$, $-S(O)_p C_{1-6}$alkyl, or $-NR_7COC_{1-6}$alkyl;

$R_{11}$ is Ar, $C_{3-8}$cycloalkyl, $C_{1-8}$alkyl, $C_{2-8}$alkenyl, $C_{2-8}$alkynyl all of which may be unsubstituted or substituted by one or more OH, $CH_2OH$, $N(R_6)_2$ or halogen;

Ar is:

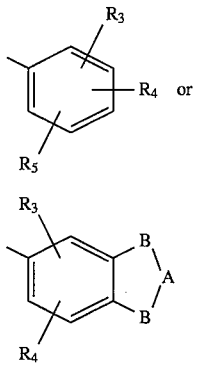

naphthyl, indolyl, pyridyl, thienyl, oxazolidinyl, oxazolyl, thiazolyl, benzoyl, isothiazolyl, pyrazolyl, triazolyl, tetrazolyl, imidazolyl, imidazolidinyl, furyl, thiazolidinyl, isoxazolyl, oxadiazolyl, thiadiazolyl, morpholinyl, piperidinyl, piperazinyl, pyrrolyl, or pyrimidyl; all of which may be unsubstituted or substituted by one or more $R_3$ or $R_4$ groups;

A is C=O, or $[CCR_6)_2]_m$;

B is $-CH_2-$ or $-O-$;

n is 0 to 6;

m is 1 or 2;

p is 0, 1 or 2;

and the dotted line indicates the optional presence of a double bond; or a pharmaceutically acceptable salt thereof, provided $R_{10}$ is not H when $R_1$, $R_2$ and $R_{11}$ are all unsubstituted phenyl and $R_8$ is COOH, and X is $(CH_2)_n$ when n= 0 and $R_8$ is COOH.

Also included in the invention are pharmaceutically acceptable salt complexes of the compounds of this invention which can form salts.

All defined alkyl, alkenyl and alkoxy groups may be straight or branched. The term "halogen" is used to mean iodo, fluoro, chloro or bromo.

The compounds of the present invention may contain one or more asymmetric carbon atoms and may exist in racemic and optically active form. All of these compounds and all geometrical isomers are contemplated to be within the scope of the present invention.

Preferred compounds are those in which $R_8$ is COOH; $R_1$ is (b); p is 1; $R_{10}$ is H; $R_{11}$ is imidazolyl or phenyl, $R_2$ is (a); $R_3$, $R_4$ and $R_5$ are independently MeO, $-O(CH_2)_m R_8$, or XAr optionally substituted with COOH and $R_2$ is substituted in the ortho position.

The following compounds are preferred:

(2E)-3-(2-n-Butyl-1H-imidazol-4(5)-yl)-3-(2,4-dimethoxyphenyl)-2-( 3,4-methylenedioxybenzyl)prop-2-enoic acid;

(2R,S)-3,3-Bis-(4-methoxyphenyl)-2-(3,4-methylenedioxybenzyl)propionic acid;

3,3-Diphenyl-2-(3,4-methylenedioxybenzyl)prop-2-enoic acid;

3,3-Bis-(4-methoxyphenyl)-2-(3,4-methyleneclioxybenzyl)prop-2-enoic acid;

3,3-Bis-(3,4-methylenedioxyphenyl)-2-(3,4-methylenedioxybenzyl)prop-2-enoic acid.
(2E)-3-(2-n-Butyl-1-methyl-1H-imidazol-5-yl)-3-(2-carboxymethoxy-4-methoxyphenyl)-2-(3,4-methylenedioxybenzyl)prop-2-enoic acid.
(2E)-3-(2-n-Butyl-1-trimethylsilylethyloxymethoxy-1H-imidazol- 5-yl)-3-(2-carboxymethoxy-4-methoxyphenyl)-2-(3,4-methylenedioxybenzyl)prop-2-enoic acid.
(2Z)-Methyl-3-(2-Carboxymethoxy-4-methoxyphenyl)-3-phenyl- 2-(3,4-methylenedioxybenzyl)prop-2-enoate.
(2Z)-3-(2-Carboxymethoxy-4-methoxyphenyl)-3-phenyl-2-( 3,4-methylenedioxybenzyl)prop-2-enoic acid
(2E)-3-(2-Carboxymethoxy-4-methoxyphenyl)-3-phenyl-2-( 3,4-methylenedioxybenzyl)prop-2-enoic acid
(2E)-3-(2-n-Butyl-1-methyl-1H-imidazol-5-yl)-3-(2,4-dimethoxyphenyl)-2-(3,4-methylenedioxybenzyl)prop-2-enoic acid The present invention provides compounds of formula (I) above:

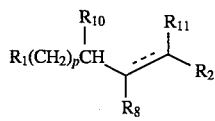   1

Those compounds in which $R_8$ is $CO_2H$ can be prepared by a process which comprises:
reacting an aldehyde of formula (2)

$R_{11}$—CHO    2 with a Grignard reagent of formula (3) wherein X is halogen, in a suitable solvent such as tetrahydrofuran at room temperature.

$R_2$—MgX    3 to provide an alcohol of formula (4).

   4

Treatment of compound (4) with a suitable oxidant such as manganese (IV) oxide in a solvent such as dichloromethane, provides a carbonyl compound of formula (5).

   5

Treatment of a carbonyl of type (5) with the lithium enolate of ester (6),

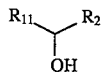   6 wherein Y is $C_{1-5}$ alkyl, prepared from ester (6) by deprotonation with a base such as lithium di-isopropylamide at $-78°$ C. in a solvent such as tetrahydrofuran under an inert atmosphere such as argon provides compound (7).

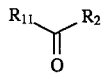   7

Esters of type (6) wherein $R_{10}$ is hydrogen and p=0 may be prepared by treatment of a benzylic halide (8) wherein X is halogen $R_1$—$CH_2X$    8 with the sodium salt of a dialkylmalonate in a suitable solvent such as acetonitrile to provide compounds of formula (9).

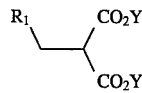   9

Saponification with a base such as aqueous sodium hydroxide in a solvent such as methanol at reflux, followed by acidification with aqueous hydrochloric acid affords di-acids of type (10).

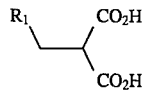   10

Subsequent thermolysis at approximately 200° C. leads to decarboxylation providing acid (11).

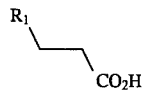   11

The acid (11) may then be esterified by treatment with an alcohol YOH wherein Y is $C_{1-5}$ alkyl in the presence of a suitable acid such as sulfuric. Alternatively treatment of (11) with a base such as 1,8-diaza-bicyclo[5.4.0]undec-7-ene in a solvent such as acetonitrile followed by the addition of a suitable alkyl halide YX affords esters of type (6)($R_{10}$=H, p=0).
Alternatively esters of type (6) wherein p=0 may be prepared by reaction of a carbonyl compound such as (12)

   12 with a bromo ester such as (13) in the presence of a metal such as zinc to afford alcohols of formula (13).

Br—$CH_2CO_2Y$    13

   14

Alternatively alcohols of formula (14) may be prepared from carbonyl compounds of type (12) by treatment at $-78°$ C. in a solvent such as tetrahydofuran under an inert atmosphere such as argon,with the lithium enolate derived from alkyl acetates (prepared by deprotonation of the acetate with lithium di-isopropylamide at $-78°$ C. in a solvent such as tetrahydrofuran under an inert atmosphere such as argon) followed by quenching with a dilute mineral acid such as hydrochloric.
Elimination of water from alcohols such as (14) can be achieved in the presence of an acid such as trifluoroacetic or alternatively alcoholic hydrogen chloride to afford an olefin of formula (15).

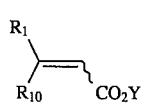   15

Alternatively for compounds of type (14) in which $R_{10}$=H, elimination can be achieved by treatment with methanesulfonyl chloride in a solvent such as dichloromethane in the presence of a suitable base such as triethylamine followed by treatment of the derived methanesulfonate with a base such as 1,8-diazabicyclo[5.4.0]undec-7-ene thus providing olefin (15).

Hydrogenation of compounds of type (15) with hydrogen gas at pressures ranging from atmospheric to approximately 60 psi. in the presence of a catalyst such as 10% palladium on charcoal in a solvent such as ethyl acetate affords esters of formula (6)(p=0).

Alternatively treatment of an olefin of type (15) with samarium II iodide in a solvent such as tetrahydrofuran containing methanol affords esters of formula (6)(p=0).

As a further alternative esters of type (6)(p=0), wherein $R_{10}$ is not hydrogen, may be prepared by Knoevenagel reaction of aldehydes of formula (16)

16 with Meldrum's acid in the presence of a base such as pyridine to provide arylidene derivatives such as (17).

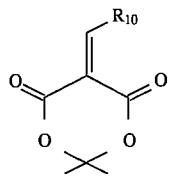

17

Treatment of arylidene derivatives such as (17) with Grignard compounds of formula (18)

18 in a solvent such as diethyl ether at approximately 0° C. affords compounds of formula (19)

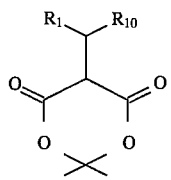

19

Reaction of compounds of formula (19) with an alcohol YOH in the presence of pyridine and copper powder affords esters of type (6)(p=0, $R_{10}$ is not H). Esters of formula (6) wherein p=1 may be prepared from the corresponding ester wherein p=0 by saponification with a base such as aqueous sodium hydroxide in a solvent such as methanol affording an acid of formula (20)

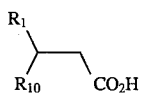

20

Alternatively treatment of an alkylated Meldrum's acid derivative such as (19) with an acid such as hydrochloric provides an acid of type (20) directly. Reaction of an acid of formula (20) with thionyl chloride or alternatively oxalyl chloride or as a further alternative triphenylphosphine and carbon tetrachloride provides an acid chloride of type (21).

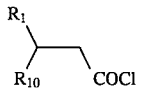

21

Reaction of an acid chloride of formula (21) with diazomethane in a solvent such as ether affords diazo ketones of structure (22).

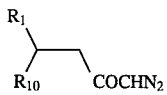

22

Treatment of diazo ketones of type (22) with silver (I) oxide in the presence of an alcohol YOH affords the homologated ester of formula (6)(p=1). Alternatively photolysis of diazoketones of formula (22) in the presence of an alcohol YOH provides esters of type (6)(p=1).

An alternative route to esters of type (6) wherein p= 1, proceeds via reduction of an ester of formula (6) (p=0) with a reducing agent such as lithium aluminum hydride in a solvent such a tetrahydrofuran to provide an alcohol of structure (23).

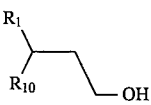

23

An alcohol of type (23) may aim be prepared by reduction of an acid of formula (20) with a reducing agent such as diborane in a solvent such as tetrahydrofuran. Reaction of an alcohol of formula (23) with methanesulfonyl chloride in the presence of a base such as triethylamine in a suitable solvent such as dichloromethane produces the methanesulfonate (24).

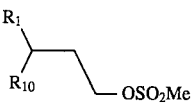

24

Treatment of a compound such as (24) with sodium or potassium cyanide in a solvent such as dimethylformamide affords nitriles of formula (25).

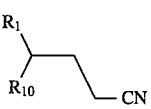

25

Hydrolysis of nitriles of formula (25) can be achieved by treatment with a base such as aqueous sodium hydroxide in the presence of hydrogen peroxide to produce an acid of type (26) following acidification with a mineral acid such as hydrochloric.

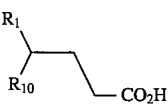

26

Alternatively carboxylic acids of formula (26) can be obtained by treatment of nitriles of type (25) with a mineral acid such as hydrochloric. The acid (26) may then be esterified by treatment with an alcohol YOH in the presence of a suitable acid such as sulfuric. Alternatively treatment of (26) with a base such as 1,8-diazabicyclo[5.4.0]undec-7-ene in a solvent such as acetonitrile followed by the addition of a suitable alkyl halide YX affords esters of type (6)(p= 1). Treatment of compound (7) with a suitable acid such as trifluoroacetic acid or alternatively hydrogen chloride in methanol affords a mixture of olefins of formula (27) which may be separated chromatographically.

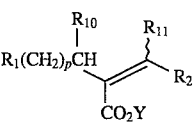

27

Alternatively reaction of a compound of formula (5) with Lawessons Reagent [2,4-bis(4-methoxyphenyl)-1,3-dithia-2,4-diphosphetane-2,4-disulfide] in a suitable solvent such as tetrahydrofuran at room temperature affords a thione of formula (28).

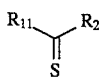

28

Reaction of a compound of formula (28) with a diazoester of formula (29), wherein Y is $C_{1-5}$ alkyl,

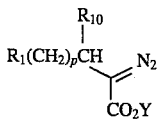

29 in refluxing tetrahydrofuran affords thiirane (30).

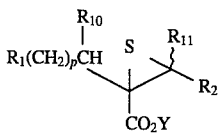

30

A diazo ester of formula (29) can be prepared from the corresponding ester (6) by treatment with lithium di-isopropylamide at −78° C. under an inert atmosphere in a solvent such as tetrahydrofuran followed by the addition of ethyl formate to produce a formylated ester of structure (31).

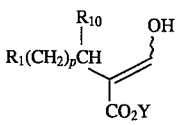

31

Treatment of a compound of formula (31) with an arylsulfonylazide such as 4-carboxyphenylsulfonyl azide in the presence of a base such as triethylamine followed by in situ treatment with a base such as aqueous potassium hydroxide provides diazoesters of type (29).

Treatment of a thiirane of formula (30) with trimethylphosphite in a suitable solvent such as chloroform at reflux affords the mixture of olefins of formula (32) which may be separated chromatographically.

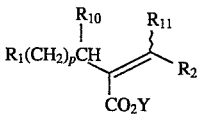

32

Alternatively the diastereomeric thiiranes (30) may be separated chromatographically and individually converted to single geometrical isomers of an olefin of formula (32).

Treatment of a single geometrical isomer of an olefin ester of formula (32) with a base such as sodium hydroxide in a suitable solvent such as aqueous propan-2-ol at reflux, followed by acidification affords a single geometrical isomer of an acid of formula (33).

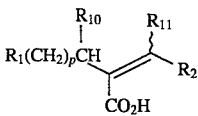

33

Hydrogenation of a compound of formula (33) with hydrogen gas at approximately 60 psi in the presence of a suitable catalyst such as 10% palladium on charcoal provides an acid of formula (34).

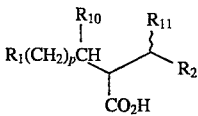

34

Alternatively reaction of an acrylate ester of type (32) with samarium II iodide in a suitable solvent such as tetrahydrofuran containing an alcohol such as methanol affords an ester of formula (35) as a mixture of diastereoisomers.

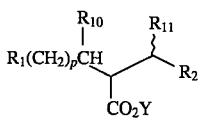

35

Saponification of an ester of formula (35) can be achieved by treatment with a base such as sodium hydroxide in a solvent such as aqueous methanol to provide an acid of type (34). To synthesize compounds of type (1) wherein $R_8$ is tetrazole, acids of type (33) or (34) may be converted to amides of structure (36) by treatment with thionyl chloride at ambient temperature, followed by evaporation to yield the acid chloride, which can then be reacted with aqueous ammonia to provide amides of formula (36).

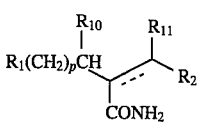

36

An amide of formula (36) can be treated with oxalyl chloride in dimethyl formamide at 0° C. to provide the nitriles of formula (37).

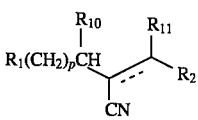

37

Reaction of a nitrile of type (37) with aluminum azide in a suitable solvent such as tetrahydrofuran at reflux affords a tetrazole of formula (38).

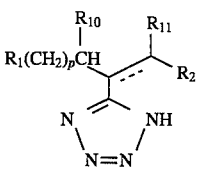

38

In order to use a compound of the Formula (I) or a pharmaceutically acceptable salt thereof for the treatment of humans and other mammals it is normally formulated in accordance with standard pharmaceutical practice as a pharmaceutical composition.

Compounds of Formula (I) and their pharmaceutically acceptable salts may be administered in a standard manner for the treatment of the indicated diseases, for example orally, parenterally, sublingually, transdermally, rectally, via inhalation or via buccal administration.

Compounds of Formula (I) and their pharmaceutically acceptable salts which are active when given orally can be formulated as syrups, tablets, capsules and lozenges. A syrup formulation will generally consist of a suspension or solution of the compound or salt in a liquid carrier for example, ethanol, peanut oil, olive oil, glycerine or water with a flavouring or colouring agent. Where the composition is in the form of a tablet, any pharmaceutical carrier routinely used for preparing solid formulations may be used. Examples of such carders include magnesium stearate, terra alba, talc, gelatin, agar, pectin, acacia, stearic acid, starch, lactose and sucrose. Where the composition is in the form of a capsule, any routine encapsulation is suitable, for example using the aforementioned carriers in a hard gelatin capsule shell. Where the composition is in the form of a soft gelatin shell capsule any pharmaceutical career routinely used for preparing dispersions or suspensions may be considered, for example aqueous gums, celluloses, silicates or oils and are incorporated in a soft gelatin capsule shell.

Typical parenteral compositions consist of a solution or suspension of the sterile compound or salt in a sterile aqueous or non-aqueous carrier optionally containing a parenterally acceptable oil, for example polyethylene glycol, polyvinylpyrrolidone, lecithin, arachis oil, or sesame oil.

Typical compositions for inhalation are in the form of a solution, suspension or emulsion that may be administered as a dry powder or in the form of an aerosol using a conventional propellant such as dichlorodifluoromethane or trichlorofluoromethane.

A typical suppository formulation comprises a compound of Formula (1) or a pharmaceutically acceptable salt thereof which is active when administered in this way, with a binding and/or lubricating agent, for example polymeric glycols, gelatins, cocoa-butter or other low melting vegetable waxes or fats or their synthetic analogues.

Typical transdermal formulations comprise a conventional aqueous or non-aqueous vehicle, for example a cream, ointment, lotion or paste or are in the form of a medicated plaster, patch or membrane.

Preferably the composition is in unit dosage form, for example a tablet, capsule or metered aerosol dose, so that the patient may administer to himself a single dose.

Each dosage unit for oral administration contains suitably from 0.1 mg to 500 mg and preferably from 1 mg to 100 mg and each dosage unit for parenteral administration contains suitably from 0.1 mg to 100 mg, of a compound of Formula (I) or a pharmaceutically acceptable salt thereof calculated as the free acid. Each dosage unit for intranasal administration contains suitably 1–400 mg and preferably 10 to 200 mg per person. A topical formulation contains suitably 0.01 to 1.0% of a compound of Formula (I).

The daily dosage regimen for oral administration is suitably about 0.01 mg/Kg to 40 mg/Kg, of a compound of Formula (I) or a pharmaceutically acceptable salt thereof calculated as the free acid. The daily dosage regimen for parenteral administration is suitably about 0.001 mg/Kg to 40 mg/Kg, of a compound of the Formula (I) or a pharmaceutically acceptable salt thereof calculated as the free acid. The daily dosage regimen for intranasal administration and oral inhalation is suitably about 10 to about 500 mg/person. The active ingredient may be administered from 1 to 6 times a day, sufficient to exhibit the desired activity.

No unacceptable toxicological effects are expected when compounds of the invention are administered in accordance with the present invention.

The biological activity of the compounds of Formula (I) are demonstrated by the following tests:

I. BINDING ASSAY

A) Membrane Preparation

Rat cerebellum or kidney cortex were rapidly dissected and frozen immediately in liquid nitrogen or used fresh. The tissues, 1–2 g for cerebellum or 3–5 g for kidney cortex, were homogenized in 15 mls of buffer containing 20 mM Tris HCl and 5 mM EDTA, pH 7.5 at 4° C. using a motor-driven homogenizer. The homogenates were filtered through cheesecloth and centrifuged at 20,000× g for 10 minutes at 4° C. The supernatant was removed and centrifuged at 40,000×g for 30 minutes at 4° C. The resulting pellet was resuspended in a small volume of buffer containing 50 mM Tris, 10 mM $MgCl_2$, pH 7.5; aliquotted with small vials and frozen in liquid nitrogen. The membranes were diluted to give 1 and 5 mg of protein for each tube for cerebellum and kidney cortex in the binding assay.

Freshly isolated rat mesenteric artery and collateral vascular bed were washed in ice cold saline (on ice) and lymph nodes were removed from along the major vessel. Then, the tissue was homogenized using a polytron in buffer containing 20 mM Tris and 5 mM EDTA, pH 7.5 at 4° C. in 15 ml volume for ~6 gm of mesenteric artery bed. The homogenate was strained through cheesecloth and centrifuged at 2,000×g for 10 min. at 4° C. The supernatant was removed and centrifuged at 40,000×g for 30 min. at 4° C. The resulting pellet was resuspended as explained above for cerebellum and kidney cortex. Approximately 10 mg of membrane protein was used for each tube in binding experiments.

B) $[^{125}I]$ET-1 Binding Protocol $[^{125}I]$ET-1 binding to membranes from rat cerebellum (2–5 mg protein/assay tube) or kidney cortex (3–8 mg protein/assay tube) were measured after 60 minutes incubation at 30° C. in 50 mM Tris HCl, 10 mM $MgCl_2$, 0.05% BSA, pH 7.5 buffer in a total volume of 100 ml. Membrane protein was added to tubes containing either buffer or indicated concentration of compounds. [$^{125}I$]ET-1 (2200 Ci/mmol) was diluted in the same buffer containing BSA to give a final concentration of 0.2–0.5 nM ET-1. Total and nonspecific binding were measured in the absence and presence of 100 nM unlabelled ET-1. After the incubation, the reactions were stopped with 3.0 ml cold buffer containing 50 mM Tris and 10 mM $MgCl_2$, pH 7.5. Membrane bound radioactivity was separated from free ligand by filtering through Whatman GF/C filter paper and washing the filters 5 times with 3 ml of cold buffer using a Brandel cell harvester. Filter papers were counted in a gamma counter with an efficiency of 75%. $IC_{50}$'s for the compounds of this invention range from 0.1 nm to 50 μm.

II. IN VITRO VASCULAR SMOOTH MUSCLE ACTIVITY

Rat aorta are cleaned of connective tissue and adherent fat, and cut into ring segments approximately 3 to 4 mm in length. Vascular rings are suspended in organ bath chambers (10 ml) containing Krebs-bicarbonate solution of the following composition (millimolar): NaCl, 112.0; KCl, 4.7; $KH_2PO_4$, 1.2; $MgSO_4$, 1.2; $CaCl_2$, 2.5; $NaHCO_3$, 25.0; and dextrose, 11.0. Tissue bath solutions are maintained at 37° C. and aerated continuously with 95% $O_2$/5% $CO_2$. Resting tensions of aorta are maintained at 1 g and allowed to equilibrate for 2 hrs., during which time the bathing solution is changed every 15 to 20 min. Isometric tensions are recorded on Beckman R-611 dynographs with Grass FT03 force-displacement transducer. Cumulative concentration-response curves to ET-1 or other contractile agonists are constructed by the method of step-wise addition of the agonist. ET-1 concentrations are increased only after the previous concentration produces a steady-state contractile response. Only one concentration-response curve to ET-1 is generated in each tissue. ET receptor antagonists are added to paired tissues 30 min prior to the initiation of the concentration-response to contractile agonists.

ET-1 induced vascular contractions are expressed as a percentage of the response elicited by 60 mM KCl for each individual tissue which is determined at the beginning of each experiment. Data are expressed as the mean ± S.E.M. Dissociation constants ($K_B$) of competitive antagonists were determined by the standard method of Arunlakshana and Schild. The potency range for compounds of this invention range from 0.1 nM to 50 μM.

The following examples are illustrated and are not limiting of the compounds of this invention.

EXAMPLE 1

(2E)-3-(2-n-Butyl-1H-imidazol-4(5)-yl)-3-(2,4-dimethoxyphenyl)-2-(3,4-methylenedioxybenzyl)prop-2-enoic acid a) 2-n-Butyl-1H-imidazole-4(5)-carbaldehyde To a stirred solution of 2-n-butyl-4(5)-hydroxymethyl-1H-imidazole (10 g, 64.94 mmol) dissolved in 300 ml of acetone and 300 ml of methylene chloride was added 30 g. of activated manganese dioxide and the mixture stirred at ambient temperature under argon for 18 hours. The mixture was filtered through celite and the filter bed rinsed with $CH_2Cl_2$ (3×30 ml). The crude oil was recrystallized from EtOAc/hexanes to afford the title compound (7.46 g, 75%).

b) 2-n-Butyl-4(5)-(2,4-dimethoxybenzoyl)-1H-imidazole

To dry Mg turnings (2.92 g, 120 mmol) under an Argon atmosphere at ambient temperature was added portionwise a solution of 1-bromo-2,4-dimethoxybenzene (17.3 ml, 120 mmol) in 1:4 THF/$Et_2O$ (120 ml). The mixture was gently warmed until bubbles formed, heating was removed and the reaction stirred for 3 hrs. As the reaction proceeded the mixture separated into 2 layers: addition of THF (47 ml) returned this to a single layer. A portion (33 ml, 20 mmol) of the resulting 2,4-dimethoxy-phenyl magnesium bromide solution was added dropwise to a solution of 2-n-butyl-1H-imidazole-4(5)-carbaldehyde (1.52 g, 10 mmol) in THF (60 ml) under Argon at ambient temperature. After stirring for 30 min. the reaction mixture was poured into cold aq. $NH_4Cl$, $CH_2Cl_2$ was added and the aqueous layer acidified to pH 6.4 with HOAc. The layers were separated and the aqueous layer further extracted with $CH_2Cl_2$. The combined organic layers were dried ($MgSO_4$ anhydrous), filtered and treated directly with $MnO_2$ (9.5 g, 100 mmol). The reaction was stirred at ambient temperature for 18 hrs. under argon then filtered (see previous preparation) to afford crude ketone (5 g). The product was chromatographed on silica gel (elutant:3% acetone/$CHCl_3$) to provide the title compound (2.29 g, 80%).

c) 1-t-Butoxycarbonyl-2-n-butyl-4-(2,4-dimethoxybenzoyl)-1H-imidazole.

To a stirred solution of 2-n-butyl-4(5)-(2,4-dimethoxybenzoyl)-1H-imidazole (2.29 g, 7.94 mmol) in acetonitile (50 ml) at ambient temperature was added 4-dimethylaminopyridine (102 mg, 0.834 mmol) followed by di-t-butyl dicarbonate (1.82 g, 8.34 mmol. The reaction was stirred for 4 hours then partitioned between EtOAc and $H_2O$ after partially removing the acetonitrile in vacuo. The aqueous layer was extracted with EtOAc and the combined organic portions were washed twice with aqueous $KH_2PO_4$ and brine. After drying ($MgSO_4$ anhydrous) evaporation under reduced pressure gave the title compound. (3.0 g, 97%)

d) 1-t-Butoxycarbonyl-2-n-butyl-4-(2,4-dimethoxythiobenzoyl)-1H-imidazole, 1-t-Butoxycarbonyl-2-n-butyl-4-(2,4-dimethoxybenzoyl)-1H-imidazole (388 mg, 1 mmol) dissolved in toluene (2 ml) was treated with 2,4-bis(4-methoxyphenyl)-1,3-dithia- 2,4-diphosphetane-2,4-disulfide (Lawesson's reagent) (222 mg,0.55 mmol) and heated to 65° for 1 hr under Argon. The reaction was cooled and the toluene solution applied directly to a silica gel column and eluted with EtOAc/hexanes (12.5% to 25%) to afford the title compound as a bright blue oil. (348 mg, 86%).

e) Methyl (2RS,3RS) and (2RS,3SR)-3-(1-t-Butoxycarbonyl-2-n-Butyl-1H-imidazol- 4-yl)-3-(2,4-dimethoxyphenyl)-2-(3,4-methylenedioxybenzyl)thiirane- 2-carboxylate.

The freshly prepared 1-t-butoxycarbonyl-2-n-butyl-4-(2,4-dimethoxythiobenzoyl)-1H-imidazole (348 mg, 0.86 mmol) was coupled to methyl- 2-diazo-3-(3,4-methylenedioxyphenyl)propionate (222 mg, 0.95 mmol) by stirring in $Et_2O$ (10 ml) under argon at ambient temperature for 18 hrs. The $Et_2O$ was evaporated under reduced pressure and the residue containing the title mixture of thiiranes was used without purification. (412 mg, 78%).

f) Methyl 2-Formyl-3-(3,4-methylenedioxyphenyl)propionate.

To a stirred solution of di-isopropylamine (1 ml,7.14 mmol) in dry THF (6 ml) at 0° C. under argon was added n-BuLi in hexane (2.64 ml, 2.5M, 6.6 mmol). After 15 min. the solution was cooled to −78° C. and methyl 3-(3,4-methylenedioxyphenyl)propionate (1.248 g, 6 mmol) in dry THF (6 ml) was added dropwise over 15 min. After a further 5 min stirring ethyl formate (2.42 ml, 30 mmol) was added dropwise. The mixture was stirred at −78° C. for 1 hr, warmed to 0° C., poured into 1M aq. HCl and extracted with EtOAc (3X). The organic extract was washed with water then brine, dried ($MgSO_4$ anhydrous) filtered and evaporated to give an oil (1.74 g). The product was purified by low pressure column chromatography on silica gel (eluant: 12.5% $Et_2O$/hexane) to give the title compound as a colorless oil (0.987 g, 70%).

g) Methyl-2-Diazo-3-(3,4,methylenedionxyphenyl)-propionate.

To a solution of methyl 2-formyl-3-(3,4-methylenedioxyphenyl)propionate (0.987 g, 4.18 mmol) in $CH_3CN$ (13 ml) and triethylamine (1.75 ml, 12.56 mmol) at −15° C. was added portionwise 4-carboxyphenylsulfonyl azide (0.95 g, 4.18 mmol). The mixture was stirred at −15° C. for 3 hr then warmed to −5° C. and aqueous potassium hydroxide added (4.5 ml, 1M, 4.5 mmol). The cooling bath was removed and the reaction stirred for 10 min. The product was partitioned between $CH_2Cl_2$ and water. The organic extract was washed with 0.5M aqueous KOH then dried ($Na_2SO_4$ anhydrous), filtered and evaporated. Chromatography on silica-gel (eluant: 12.5% EtOAc/hexane) gave the title compound as a yellow oil (0.803 g, 82%), which was stored below 4° C.

h) Methyl(2E,Z)-3(1-t-Butoxycarbonyl-2-n-Butyl-1H-imidazol-4-yl)-3-( 2,4-dimethoxyphenyl)-2-(3,4-methylenedioxybenzyl)prop-2-enoate.

Methyl (2RS,3RS) and (2RS,3SR)-3-(1-t-Butoxycarbonyl-2-n-Butyl- 1H-imidazol-4-yl)-3-(2,4-dimethoxyphenyl)-2-(3,4-methylene-dioxybenzyl)thiirane- 2-carboxylate(372 mg, 0.61 mmol) and trimethyl phosphite (1 ml, 8 mmol) in $CHCl_3$ were kept at reflux temperature for 55 hrs. The solvent and excess trimethylphosphite were removed under reduced pressure (high vacuum) and the residue chromatographed on silica gel (15%–25% EtOAc/hexanes) to give a mixture of geometrical isomers of the title compound as one spot. (352 mg, quantitative) Hplc separation of the isomers was accomplished on 1" semi-prep Dynamax Reverse Phase column (80% $CH_3CN/H_2O$, 19 ml/min) with first isomer (Z) eluting at 33 minutes and the (E)- isomer at 46 min.

i) (2E)-3-(2-n-Butyl-1H-imidazol-4(5)-yl)-3-(2,4-dimethoxyphenyl)- 2-(3,4-methylenedioxybenzyl)prop-2-enoic acid Methyl-(2E)-3-(1-t-Butoxycarbonyl-2-n-Butyl-1H-imidazol-4-yl)-3-( 2,4-dimethoxyphenyl)-2-(3,4-methylenedioxybenzyl)prop-2-enoate (17.8 mg, 0.031 mmol) in 0.3 ml 2.5N NaOH and 0.3 ml isopropanol was heated under Argon at 100° for 55 hours. The solvent (i-PrOH) was removed under reduced pressure and the residue was diluted with $H_2O$ and washed with EtOAc, which was discarded. The pH was lowered to 5.2 with 1M HCl and the solution was extracted with EtOAc. The combined extracts were dried ($Na_2SO_4$ anhydrous) and evaporated. (9.7 mg, 69% ). The crude title compound was recrystallized from EtOAc/hexanes to afford a tan solid. (5.1 mg, 36%).

$^1H$ NMR ($CDCl_3$): δ7.10 (br s, 1H); 6.95 (d, 1H, J= 8.4 Hz); 6.90 (d, 1H, J= 8.0 Hz); 6.71 (d, 1H, J= 7.94 Hz); 6.51 (s, 1H ); 6.50 (s, 1H); 5.91 (s, 2H); 4.45 (br s, 2H); 3.80 (s, 3H); 3.67 (s, 3H); 2.65 (apparent t, 2H, J= 7.4 Hz, J= 7.6 Hz); 1.67 (dt, 2H, J= 7.4 Hz, J= 15 Hz); 1.33 (m, 2H); 0.88 (t, 3H, J= 7.4 Hz).

NOE ($CDCl_3$): observed between $CH_2$ and Imidazole CH.

IR (KBr pellet): 1684 $cm^{-1}$ (weak br), 1609 $cm^{-1}$

MS (DCI $CH_4$) m/e: 493.2 $(M+C_2H_5)^+$, 465.1 $(M+H)^+$ (exact mass) $M^+$: 464.1959 (Δ= 1.1 mDa for $C_{26}H_{28}N_2O_6$)

Anal. Calc. for $C_{18}H_{20}N_2O_4·¾H_2O$: C, 69.19; H, 5.92. Found: C, 68.90, 68.87; H, 5.63, 5.65.

EXAMPLE 2

(2R,S)-3,3-Bis-(4-methoxyphenyl)-2-(3,4-methylenedioxybenzyl)propionic acid a) Methyl (2R,S)-3,3-Bis-(4-methoxyphenyl)-2-( 3,4-methylenedioxybenzyl)propionate Methyl 3,3-Bis-(4-methoxyphenyl)-2-(3,4-methylenedioxybenzyl)prop-2-enoate (76 mg, 0.18 mmol) was dissolved in MeOH (0.5 ml) and a solution of samarium II iodide in THF (16 ml, 0.1M, 1.6 mmol) added dropwise with stirring under argon. The product was partitioned betweeen EtOAc and 1M aqueous HCl. The organic extract was washed with aqueous $Na_2S_2O_3$ and then brine. After drying ($MgSO_4$ anhydrous), filtration and evaporation gave the title compound as a pale-yellow solid (79 mg) which was chromatographed on silica gel (elutant 12.5%, EtOAc/hexanes) to provide the title compound (0.06 g, 79%).

b) (2R,S)-3,3-Bis-(4-methoxyphenyl)-2-(3,4-methylenedioxybenzyl)propionic acid

Methyl (2R,S)-3,3-Bis-(4-methoxyphenyl)-2-( 3,4-methylenedioxybenzyl)propionate (0.06 g, 0.14 mmol) was dissolved in isopropanol (2 ml) and 5M aqueous NaOH (2 ml, 10 mmol) added. The mixture was refluxed for 55 h then cooled and acidified with 1M aqueous HCl. The product was extracted with EtOAc. The organic extract was dried ($MgSO_4$ anhydrous), filtered and evaporated. The product was purified by column chromatography on silica-gel (elutant:6–10% MeOH/$CHCl_3$) to give, after lyophylization, the title compound as a white solid (29 mg, 45%).

$^1H$ NMR ($CDCl_3$): δ7.25–7.18 (dd, 4H); 6.86 (d, 2H, J= 8.7 Hz); 6.73 (d, 2H, J= 8.7 Hz); 6.63 (d, 1H, J= 7.9 Hz); 6.55 (d, 1H, J= 1.5 Hz); 6.49 (dd, 1H, J=7.9 Hz, J= 1.5 Hz); 5.86 (s, 2H); 4.02 (d, 1H, J= 11.6); 3.78 (s, 3H); 3.69 (s, 3H); 3.36 (ddd, 1H); 2.60 (m, 2H).

IR (Nujol mull): 1740 $cm^{-1}$, 1710 $cm^{-1}$.

MS m/e: 449.2 $(M+C_2H_5)^+$, 420.2 $M^+$

Anal. Calc. for $C_{25}H_{24}O_6·¾H_2O$: C, 69.19; H, 5.92. Found: C, 68.90, 8.87; H, 5.63, 5.65.

EXAMPLE 3

3,3-Diphenyl-2-(3,4-methylenedioxybenzyl)prop-2-enoic acid a) Methyl(2RS)-3,3-Diphenyl-3-hydroxy-2-( 3,4-methylenedioxybenzyl)propanoate To a solution of di-isopropylamine (0.52 ml, 3.69 mmol) in dry THF (3 ml) at 0° C. under argon was added n-BuLi in hexane (1.36 ml, 2.5 M, 3.4 mmol). After stirring for 40 min the solution was cooled to −78° C. and a solution of methyl 3-( 3,4-methylenedioxyphenyl)-propanoate (0.592 g, 2.84 mmol) in dry THF (2 ml) was added dropwise over 7 min. After a further 2 min a solution of benzophenone (0.517 g, 2.84 mmol) in dry THF (2 ml) was added dropwise. After a further 30 min at −78° C. the mixture was warmed to 0° C. over 30 min and poured into 1M aqueous HCl. The product was extracted with EtOAc (3X). The combined organic extract was washed with water (2X) then brine. After drying ($Na_2SO_4$ anhydrous), filtration and evaporation gave an off-white solid. Recrystallization from hot hexane gave the title compound (0.835 g, 76% yield) as a colorless solid.

b) Methyl 3,3-Diphenyl-2-(3,4-methylenedioxybenzyl)prop-2-enoate

Methyl (2RS)-3,3-diphenyl-3-hydroxy-2-(3,4-methylenedioxybenzyl)propanoate (0.309 g, 0.79 mmol) was dissolved in methanolic HCl (60 ml) (prepared by passing HCl gas through MeOH at 0° C.). After 4 days at ambient temperature the MeOH was removed by evaporation and replaced with fresh methanolic HCl. After a further 2 days the methanol was evaporated. The residue was recrystallized (MeOH) to give the title compound as a colorless solid (69 mg, 23%).

c) 3,3-Diphenyl-2-(3,4-methylenedioxybenzyl)prop-2-enoic acid

Methyl 3,3-diphenyl-2-(3,4-methylenedioxybenzyl)prop-2-enoate (0.05 g, 0.13 mmol) was dissolved in EtOH (2 ml) and 3M aqueous NaOH added (2 mi, 6 mmol). After stirring at 80° C. for 15 h the EtOH was removed in vacuo and the residue partitioned between EtOAc and $H_2O$. The aqueous layer was acidified to pH 2 with 1-M-aqueous HCl and extracted with EtOAc (3X). The combined organic extract was washed with brine, dried ($MgSO_4$ anhydrous), filtered and evaporated to give a colorless solid. Recrystallization from EtOAc/hexane gave the title compound as a colorless solid (0.037 g, 77%).

$^1H$ NMR ($CDCl_3$): δ7.16–7.31 (m, 10H); 6.70–6.75 (m, 3H); 5.94 (s, 2H); 3.70 (s, 2H).

IR (KBr pellet): 1705 $cm^{-1}$

MS (ES +/−) m/e: 359 $(M+H)^+$, 357 $(M-H)^-$

Anal. Calc. for $C_{23}H_{18}O_4·⅓H_2O$: C, 76.31; H, 5.12. Found: C, 76.12, 76.36; H, 4.96, 4.80.

mp: 153.5°–154° C.

By the methods given above, the following compounds were made.

EXAMPLE 4

3,3-Bis-(4-methoxyphenyl)-2-(3,4-methylenedioxybenzyl)prop-2-enoic acid

The title compound was made starting with 4,4-dimethoxythiobenzophenone and methyl-2-diazo-3-(3,4-methylenedioxyphenyl)propionate.

$^1H$ NMR ($CDCl_3$): δ7.10–7.05 (apparent br t, 4H); 6.82–6.77 (apparent br t, 4H); 6.75–6.67 (m, 3H); 5.93 (s, 2H); 3.79 (s,6H); 3.72 (s, 2H).

IR (KBr pellet): 1690 $cm^{-1}$

MS m/e: 418.2 $(M^+·)$; 419, $(M+H)^+$

Anal. Calc. for C₂₅H₂₂O₆·⅓H₂O: C, 70.74; H, 5.38. Found: C, 70.83; H, 5:37.

mp: 61°–63° C.

EXAMPLE 5

3,3-Bis-(3,4-methylenedioxyphenyl)-2-(3,4-methylenedioxybenzyl)prop-2-enoic acid The title compound was made starting with piperonal and 4-bromo-1,2-methylenedioxybenzene to make the appropriate thione which is reacted with methyl-2-diazo-3-(3,4-methylenedioxyphenyl)propionate.

$^1$H NMR (CDCl₃): δ6.75–6.58 (m, 9H); 5.94 (s, 2H); 5.94 (s, 2H); 5.93 (s, 2H); 3.70 (s, 2H).

IR (film): 1690 cm⁻¹.

MS m/e: 447.2 (M+H)⁺; DCI (NH₃) m/e: 464.2 (M+NH₄)⁺

Anal. Calc. for C₂₅H₁₈O₈·⅓H₂O: C, 66.37; H, 4.16. Found: C, 66.36; H, 4.25. mp: 72° C.

EXAMPLE 6

(2E)-3-(2-n-Butyl-1-methyl-1H-imidazol-5-yl)-3-(2-carboxymethoxy-4-methoxyphenyl)-2-(3,4-methylenedioxybenzyl)prop-2-enoic acid a) 2-n-Butyl-4(5)-hydroxymethyl-5(4)-iodo-1H-imidazole To a stirred solution of 2-n-butyl-4(5)-hydroxymethyl-1H-imidazole (67.07 g, 434.9 mmol) dissolved in absolute ethanol (500 ml) was added N-iodosuccinimide (99 g, 440 mmol) and the mixture was stirred at ambient temperature under argon for 15 min., then gently warmed to 45° C. for 45 min. The mixture was cooled in an ice bath to begin crystallization of the product; then 2.5 l of H₂O was added with stirring and further chilling. The product was collected by filtration to afford, after drying (80° under vacuum), the title compound (110.61 g, 91%).

b) 2-n-Butyl-5(4)-iodo-1H-imidazole-4(5)-carbaldehyde

To a stirred solution of 2-n-butyl-4(5)-hydroxymethyl-5(4)-iodo-1H-imidazole (110 g, 392.9 mmol) dissolved in acetone (1l) and methylene chloride (5l) was added 300 g. of activated manganese dioxide and the mixture stirred at reflux temperature under argon for 18 h. The mixture was filtered through celite and the filter bed rinsed with hot CH₂Cl₂. The crude oil was crystallized from methylene chloride to afford the title compound (59 g, 54%).

c) 2-n-Butyl-4-iodo-1-methyl-1H-imidazole-5-carbaldehyde

To a stirred solution of 2-n-butyl-5(4)-iodo-1H-imidazole-4(5)-carbaldehyde (2.3 g, 8.27 mmol) in 1M tetrabutylammonium-fluoride solution in THF (82 ml, 82 mmol) containing 15 g of 5 Å molecular sieves was added dimethyl sulfate (5 ml, 52.8 mmol). The reaction was stirred at ambient temperature for 1 h., then filtered to remove the molecular sieves and partitioned between EtOAc and water. The layers were separated and the aqueous layer further extracted with EtOAc (2x). The combined organic portions were washed with water then brine, dried (MgSO₄ anhydrous), filtered, and evaporated to give an oil (3.47 g). Chromatography on silica gel (1% MeOH/CH₂Cl₂) afforded the title compound as a pale yellow solid (2.03 g, 84%).

d) 2-n-Butyl-1-methyl-1H-imidazole-5-carbaldehyde 2-n-Butyl-4-iodo-1-methyl-1H-imidazole-5-carbaldehyde (1.93 g, 6.6 mmol) dissolved in MeOH (100 ml) buffered with KOAc (850 mg) was treated with 10% Pd/C and shaken under 50 psi of H₂ for 3 h. The catalyst was removed by filtration and the MeOH removed under reduced pressure. The residue was partitioned between CH₂Cl₂ and 5% NaHCO₃ solution. The layers were separated and the aqueous portion further extracted with CH₂Cl₂ (2x). The combined organic portions were dried (MgSO₄ anhydrous), filtered, and evaporated to give the title compound as a bright yellow oil. (1.86 g, 99%)

e) 2-n-Butyl-1-methyl-5-(2-benzyloxy-4-methoxybenzoyl)-1H-imidazole

To dry Mg turnings (250 mg, 120 mmol) under an argon atmosphere at ambient temperature was added portionwise a solution of 2-benzyloxy-1-bromo-4-methoxybenzene (3.0 g, 10.2 mmol) in 1:4 THF/Et₂O (20 ml). Several crystals of I₂ were added, the mixture was gently warmed, and the reaction was stirred at reflux for 4 h. The resulting 2-benzyloxy-4-methoxyphenyl magnesium bromide solution was added dropwise to a solution of 2-n-butyl-1-methyl-1H-imidazole-5-carbaldehyde (1.00 g, 6 mmol) in THF (10 ml) under argon at ambient temperature. After stirring for 30 min., the reaction mixture was poured into cold aq. NH₄Cl, CH₂Cl₂ was added, and the aqueous layer acidified to pH 6.4 with 1N HCl. The layers were separated and the aqueous layer further extracted with CH₂Cl₂. The combined organic layers (400 ml) were dried (MgSO₄ anhydrous), filtered, and treated directly with MnO₂ (8 g, 100 mmol) and 4 Å molecular sieves (20 g. approx.). The reaction was stirred at ambient temperature for 18 h under argon then filtered (see previous preparation) to afford crude ketone. The product was chromatographed on silica gel (eluant: 50% EtOAc/hexanes) to provide recovered aldehyde (0.281 g) and the title compound (1.29 g, 79%).

f) 2-n-Butyl-1-methyl-5-(2-hydroxy-4-methoxybenzoyl)-1H-imidazole 2-n-Butyl-1-methyl-5-(2-benzyloxy-4-methoxybenzoyl)-1H-imidazole (1.29 g, 3.41 mmol) dissolved in EtOAc was treated with 10% Pd/C under H₂ (1 atm) for 10 h at ambient temperature. The catalyst was removed by filtration and the solvent removed under reduced pressure to afford the title compound as a bright yellow oil which solidified on standing (888 mg, 91%)

g) 2-n-Butyl-1-methyl-5-(2-t-butoxycarbonylmethoxy-4-methoxybenzoyl)- 1H-imidazole To a mixture of NaH (80% oil dispersion, 41 mg, 1.35 mmol, previously washed with hexanes) in DMF (4 ml) was added dropwise a solution of 2-n-butyl- 1-methyl-5-(2-hydroxy-4-methoxybenzoyl)-1H-imidazole (361 mg, 1.25 mmol) in DMF (3 ml) at 0° under argon. The cooling bath was removed and the mixture stirred for 20 min. at ambient temperature. t-Butyl bromoacetate (222 μl, 1.35 mmol) was added neat and the reaction stirred overnight. The mixture was partitioned between water and EtOAc and the layers separated. The aqueous layer was further extracted (EtOAc, 2x) and the combined organic extract was washed with water (5x) and brine. Evaporation under reduced pressure after drying (MgO₄ anhydrous) afforded the title compound as a reddish oil (465 g, 93%).

h) 2-n-Butyl-1-methyl-5-(2-t-butoxycarbonylmethoxy-4-methoxythiobenzoyl)- 1H-imidazole 2-n-Butyl-1-methyl-5-(2-t-butoxycarbonylmethoxy-4-methoxybenzoyl)-1H-imidazole (465 mg, 1.16 mmol) dissolved in toluene (5 ml) was mixed with 2,4-bis(4-methoxyphenyl)-1,3-dithia-2,4-diphosphetane-2,4-disulfide (Lawesson's reagent) (258 mg, 0.638 mmol) and the solution heated to 95° for 1 h under argon. The reaction was cooled and the toluene solution applied directly to a silica gel column. Elution with 50% EtOAc/hexanes afforded the title compound as a deep purple-green solid. (206 mg, 53%).

i) Methyl (2RS,3RS) and (2RS,3SR)-3-(2-n-Butyl-1-methyl-1H-imidazol- 5-yl)-3-(2-t-butoxycarbonylmethoxy-4-methoxyphenyl)-2-( 3,4-methylenedioxybenzyl)thiirane-2-carboxylate.

The freshly prepared 2-n-butyl-1-methyl-5-(2-t-butoxycarbonylmethoxy- 4-methoxythiobenzoyl)-1H-imidazole (206 mg, 0.49 mmol) was dissolved in ether (2 ml) and methyl-2-diazo-3-(3,4-methylenedioxyphenyl)propionate as prepared in Example 1(g) (117 mg, 0.50 mmol) was added under argon. After standing at ambient temperature for 1 week, several drops of hexanes were added to the Et$_2$O solution and the resulting white ppt (162 mg) was collected by filtration to afford the (2RS,3RS) isomer of the title compound. Further addition of hexanes and cooling afforded the (2RS,3SR) isomer as a pale pink solid (60 mg). The filtrate containing the title mixture of thiiranes was chromatographed on silica gel to afford complete separation. (167 mg, (2RS,3RS) isomer; 116 mg (2RS,3SR) isomer; 92%).

j) Methyl-(2E)-3(2-n-Butyl-1-methyl-1H-imidazol-5-yl)-3-( 2-t-butoxycarbonylmethoxy-4-methoxyphenyl)-2-( 3,4-methylenedioxybenzyl)prop-2-enoate.

Methyl (2RS,3RS)-3-(2-n-Butyl-1-methyl-1H-imidazol-5-yl)-3-( 2-t-butoxycarbonylmethoxy-4-methoxyphenyl)-2-(3,4-methyleneclioxybenzyl)thiirane- 2-carboxylate (167 mg, 0.27 mmol) and trimethyl phosphite (0.075 ml, 6 mmol) in CHCl$_3$ (2 ml) were kept at reflux temperature for 18 h. The solvent and excess trimethyl phosphite were removed under reduced pressure (high vacuum) and the residue chromatographed on silica gel (80% EtOAc/hexanes) to give the title compound. (87 mg, 55%)

k) (2E)-3(2-n-Butyl-1-methyl-1H-imidazol-5-yl)-3-(2-carboxymethoxy- 4-methoxyphenyl)-2-(3,4-methylenedioxybenzyl)prop-2-enoic acid Methyl-(E)-3(2-n-Butyl-1-methyl-1H-imidazol-5-yl)-3-( 2-t-butoxycarbonylmethoxy-4-methoxyphenyl)-2-(3,4-methylenedioxybenzyl)prop-2-enoate (85 mg, 0.144 mmol) in 2.5N NaOH (1.0 ml) and isopropanol (2.0 ml) was heated under argon at 95° for 18 hours. The solvent (i-PrOH) was removed under reduced pressure and the residue was diluted with H$_2$O and washed with EtOAc. The pH of the aqueous layer was lowered to 3.5 with 1M HCl and the solution was extracted with EtOAc (5x). The combined extracts were dried (Na$_2$SO$_4$ anhydrous) and evaporated. (48 mg, 64%). The crude title compound was recrystallized from CHCl$_3$/CH$_3$CN to afford a white solid. (26 mg, 36%).

MS m/e: 523.3, (M+H)$^+$; (exact mass) M$^+$: 523.2061 (Δ= +1.9 mDa for C$_{28}$H$_{31}$N$_2$O$_{08}$)

mp: 179°–181° C.

EXAMPLE 7

(2E)-3(2-n-Butyl-1-trimethylsilylethyloxymethoxy-1H-imidazol-5-yl)-3-(2-carboxymethoxy-4-methoxyphenyl)-2-(3,4-methylenedioxybenzyl)prop-2-enoic acid a) 5-(2-Benzyloxy-4-methoxybenzoyl)-2-n-butyl- 1-trimethylsilylethyloxymethoxy-1H-imidazole To a stirred solution of 2-n-butyl-1-trimethylsilylethyloxymethoxy-1H-imidazole (1.016 g, 4 mmol) in Et$_2$O (8 ml) was added 2.5M n-BuLi (2.0 ml, 5 mmol) and the reaction stirred at ambient temperature of 15 min. Then 2-benzyloxy-4-methoxy-benzaldehyde (969 mg, 4 mmol) in THF (4 ml) was added and the reaction quenched after 15 min. by partitioning between saturated NH$_4$Cl and methylene chloride. The mixture was separated and the aqueous layer acidified to pH 6.5–7.0 and extracted further with CH$_2$Cl$_2$ (3x). The combined organic extract was washed with water and brine and dried (Na$_2$SO$_4$ anhydrous with 4 Å sieves). The solution was treated with MnO$_2$ (3.5 g, 40 mmol) and stirred 3 d. at ambient temperature under argon. The mixture was filtered through glass filter paper and evaporated. Chromatography on silica gel (eluant: 50–80% EtOAc/hexanes) afforded 600 mg of alcohol which was again treated with MnO$_2$ (5.92 g, 68 mmol) and worked-up as before to afford the title compound (557 mg, 28%).

b) 2-n-Butyl-5-(2-hydroxy-4-methoxybenzoyl)- 1-trimethylsilylethyloxymethoxy-1H-imidazole A solution of 5-(2-Benzyloxy-4-methoxybenzoyl)-2-n-butyl- 1-trimethylsilylethyloxymethoxy-1H-imidazole (549 mg, 1.1 mmol) in EtOAc (15 ml) was stirred with 10% Pd/C (87 mg) under H$_2$ (1 atm) for 18 h. Filtration and evaporation afforded the title compound as a yellow oil (407 mg, 91% ).

c) 2-n-Butyl-5-(2-ethoxycarbonylmethoxy-4-methoxybenzoyl)- 1-trimethylsilylethyloxymethoxy-1H-imidazole To a mixture of NaH (80% oil dispersion, 33 mg, 1.1 mmol, previously washed with hexanes), in DMF (4 ml) was added dropwise a solution of 2-n-butyl- 5-(2-Hydroxy-4-methoxybenzoyl)-1-trimethylsilylethyloxymethoxy-1H-imidazole-( 404 mg, 1.00 mmol) in DMF (3 ml) at 0° under argon. The cooling bath was removed and the mixture stirred for 10 min. at ambient temperature. Ethyl bromoacetate (125 μl, 1.10 mmol) was added neat and the reaction stirred for 2 h. The mixture was partitioned between water and EtOAc and the layers separated. The aqueous layer was further extracted (EtOAc, 2x) and the combined organic extract was washed with water (5x) and brine. Evaporation under reduced pressure, after drying (MgO$_4$ anhydrous) afforded the title compound as a reddish oil (475 g, 97%).

d) 2-n-Butyl-5-(2-ethoxycarbonylmethoxy-4-methoxythiobenzoyl)- 1-trimethylsilylethyloxymethoxy-1H-imidazole 2-n-Butyl-5-(2-ethoxycarbonylmethoxy-4-methoxybenzoyl)- 1-trimethylsilylethyloxymethoxy-1H-imidazole(475 mg, 0.97 mmol) dissolved in toluene (5 ml) was mixed with 2,4-bis(4-methoxyphenyl)-1,3-dithia- 2,4-diphosphetane-2,4-disulfide (Lawesson's reagent) (215 mg, 0.532 mmol) and the solution heated to 80° for 1 h under argon. The reaction was cooled and the toluene solution applied directly to a silica gel column. Elution with 25–30% EtOAc/hexanes afforded the title compound as a deep purple-blue oil. (316 mg, 64% ).

e) Methyl (2RS,3RS) and (2RS,3SR)-3-(2-n-Butyl- 1-trimethylsilylethyloxymethoxy-1H-imidazol-5-yl)-3-( 2-ethoxycarbonylmethoxy-4-methoxyphenyl)-2-( 3,4-methylenedioxybenzyl)thiirane-2-carboxylate.

The freshly prepared 2-n-butyl-5-(2-ethoxycarbonylmethoxy- 4-methoxythiobenzoyl)-1-trimethylsilylethyloxymethoxy-1H-imidazole (675 mg, 1.33 mmol) was dissolved in THF (10 ml) and methyl 2-diazo-3-(3,4-methylenedioxyphenyl)propionate as prepared in Example 1(g) (342 mg, 1.46 mmol) added under argon. After stirring at reflux temperature for 18 h, the solvent was removed and the residue was chromatographed on silica gel (50–80% EtOAc/hexanes) to afford complete separation of the title thiiranes. (411 mg, (2RS,3RS) isomer; 279 mg (2RS,3SR) isomer; 97%).

f) Methyl-(2E)-3(2-n-Butyl-1-trimethylsilylethyloxymethoxy-1H-imidazol- 5-yl)-3-(2-ethoxycarbonylmethoxy-4-methoxyphenyl)-2-( 3,4-methylenedioxybenzyl)prop-2-enoate.

Methyl (2RS,3RS)-3-(2-n-Butyl-1-trimethylsilylethyloxymethoxy- 1H-imidazol-5-yl)-3-(2-ethoxycarbonylmethoxy-4-methoxyphenyl)-2-( 3,4-methylenedioxybenzyl)thiirane-2-carboxylate (411 mg, 0.58 mmol) and trimethyl phosphite, freshly distilled from Na (2 ml, 6 mmol) with 1-methylimidazole (100 µl) in CHCl$_3$ (4 ml) were kept at reflux temperature for 48 h under argon. The solvent and excess trimethyl phosphite were removed under reduced pressure (high vacuum) and the residue chromatographed on silica gel (80% EtOAc/hexanes) to give the title compound. (256 mg, 65%)

g) (2E)-3(2-n-Butyl-1-trimethylsilylethyloxymethoxy-1H-imidazol-5-yl)-3-( 2-carboxymethoxy-4-methoxyphenyl)-2-(3,4-methylenedioxybenzyl)prop- 2-enoic acid Methyl-(2E)-3(2-n-Butyl-1-trimethylsilylethyloxymethoxy-1H-imidazol- 5-yl)-3-(2-ethoxycarbonylmethoxy-4-methoxyphenyl)-2-( 3,4-methylenedioxybenzyl)prop-2-enoate (123 mg, 0.181 mmol) in 2.5N NaOH (2.0 ml) and isopropanol (2.0 ml) was heated under argon at 95° for 18 h. The solvent (i-PrOH) was removed under reduced pressure and the residue was diluted with H$_2$O and washed with EtOAc. The pH of the aqueous layer was lowered to 3.5–4.5 with 1M HCl and the resultant precipitate was collected and air-dried (101 mg, 88%). The crude solid was recrystallized from i-propanol to afford the hydrochloride salt of the title compound as a white solid.

MS m/e: 639.2, (M+H)$^+$; (exact mass) M$^+$: 639.2722 ($\Delta$= + 1.6 mDa for C$_{33}$H$_{43}$N$_2$O$_9$Si)

mp: 185°–187° C.

h) (2E)-3(2-n-Butyl-1H-imidazol-5-yl)-3-(2-carboxymethoxy- 4-methoxyphenyl)-2-(3,4-methylenedioxybenzyl)prop-2-enoic acid To a flask containing (2E)-3(2-n-butyl-1-trimethylsilylethyloxymethoxy- 1H-imidazol-5-yl)-3-(2-carboxymethoxy-4-methoxyphenyl)-2-( 3,4-methylenedioxybenzyl)prop-2-enoic acid (32 mg, 0.05 mmol) was added at 0° HF.pyridine (3 ml) and the reaction stirred for 15 min. The solution was diluted with water (1–2 ml), 3N HCl (1 ml), and brine (2 ml). The pH was raised to 3.5 with addition of 2.5N NaOH and the solution extracted with EtOAc (5x). The EtOAc was removed under reduced pressure and the residue taken up in water which was acidified to pH 3.5 with 1 drop of 1N HCl. The copious white ppt was collected and air dried to afford the hydrochloride salt of the title compound as a tan solid. ( 15 mg, 59% )

MS m/e: 509.2, (M+H)$^+$; (exact mass) M$^+$: 509.1940 ($\Delta$= −1.6 mDa for C$_{27}$H$_{29}$N$_2$O$_8$)

mp: partial melt 148° C., 185° C. dec.

By methods given above, the following compounds were made.

EXAMPLE 8

(2Z)-Methyl-3-(2-Carboxymethoxy-4-methoxyphenyl)-3-phenyl-2-(3,4-methylenedioxybenzyl)prop-2-enoate MS m/e: 477, (M+H)$^+$;

ms: 138°–139° C.

EXAMPLE 9

(2Z)-3-(2-Carboxymethoxy-4-methoxyphenyl)1-3-phenyl-2-( 3,4-methylenedioxybenzyl)prop-2-enoic acid MS m/e: 463, (M+H)$^+$ mp: 152°–154° C.

EXAMPLE 10

(2E)-3-(2-Carboxymethoxy-4-methoxyphenyl)-3-phenyl-2-(3,4-methylenedioxybenzyl)prop-2-enoic acid MS m/e: 461, (M−H)$^-$ (exact mass) M$^+$: 462.1316 ($\Delta$= −0.1 mDa for C$_{26}$H$_{22}$O$_8$)

mp: 168°–172° C. dec.

EXAMPLE 11

(2E)-3-(2-n-Butyl-1-methyl-1H-imidazol-5-yl)-3-(2,4-dimethoxy-phenyl)- 2-(3,4-methylenedioxybenzyl)prop-2-enoic acid MS m/e: (exact mass) M$^+$ : 478.2081 ($\Delta$= + 2.3 mDa for C$_{27}$H$_{30}$N$_2$O$_6$)

EXAMPLE 12

Formulations for pharmaceutical use incorporating compounds of the present invention can be prepared in various forms and with numerous excipients. Examples of such formulations are given below.

INHALANT FORMULATION

A compound of formula I, (1 mg to 1 00 mg) is aerosolized from a metered dose inhaler to deliver the desired amount of drug per use.

| Tablets/Ingredients | Per Tablet |
| --- | --- |
| 1. Active ingredient (Cpd of Form. I) | 40 mg |
| 2. Corn Starch | 20 mg |
| 3. Alginic acid | 20 mg |
| 4. Sodium alginate | 20 mg |
| 5. Mg stearate | 1.3 mg |
|  | 2.3 mg |

PROCEDURE FOR TABLETS:

Step 1 Blend ingredients No. 1, No. 2, No. 3 and No. 4 in a suitable mixer/blender.

Step 2 Add sufficient water portion-wise to the blend from Step 1 with careful mixing after each addition. Such additions of water and mixing until the mass is of a consistency to permit its conversion to wet granules.

Step 3 The wet mass is convened to granules by passing it through an oscillating granulator using a No. 8 mesh (2.38 mm) screen.

Step 4 The wet granules are then dried in an oven at 140° F. (60° C.) until dry.

Step 5 The dry granules are lubricated with ingredient No. 5.

Step 6 The lubricated granules are compressed on a suitable tablet press.

PARENTERAL FORMULATION

A pharmaceutical composition for parenteral administration is prepared by dissolving an appropriate amount of a compound of formula I in polyethylene glycol with heating. This solution is then diluted with water for injections (to 100 ml). The solution is then steriled by filtration through a 0.22 micron membrane filter and sealed in sterile containers.

We claim:

1. A compound of the formula:

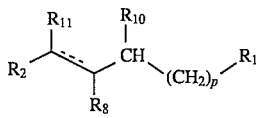
(I)

wherein:

$R_1$ and $R_2$ are independently:

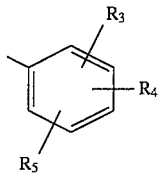
(a)

or

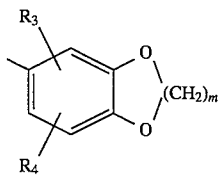
(b)

$R_3$ and $R_5$ are independently hydrogen, $R_{11}$, OH, $C_{1-8}$alkoxy, —$S(O)_pR_{11}$, —$N(R_6)_2$, Br, F, I, Cl, $CF_3$, —$NHCOR_6$, —$R_{11}CO_2R_7$, —$XR_9$—Y or —$X(CH_2)_nR_8$ wherein each methylene group within —$X(CH_2)_nR_8$ may be unsubustituted or substituted by one or two —$(CH_2)_nAr$ groups;

$R_4$ is hydrogen, $R_{11}$, OH, $C_{1-5}$alkoxy, —$S(O)_pR_{11}$, —$N(R_6)_2$, —$XR_{11}$, Br, F, I, Cl or —$NHCOR_6$ wherein the $C_{1-5}$alkoxy may be unsubustituted or substituted by OH, methoxy or halogen;

$R_6$ is independently hydrogen or $C_{1-5}$alkyl;

$R_7$ is independently hydrogen, $C_{1-10}$alkyl, $C_{2-10}$alkenyl or $C_{2-8}$alkynyl all of which may be unsubustituted or substituted by one or more OH, $N(R_6)_2$, $CO_2R_{12}$, halogen or $XC_{1-5}$alkyl; or $R_7$ is $(CH_2)_nAr$;

$R_8$ is $R_{11}$, —$CO_2R_7$, —$CO_2C(R_7)_2O(CO)XR_{11}$, —$PO_3(R_7)_2$, —$SO_2NR_7R_{11}$, —$CONR_7SO_2R_{11}$, —$SO_3R_7$, —$SO_2R_7$, —$P(O)(OR_7)R_7$, CN, —$NR_7SO_2R_{11}$, —$C(O)N(R_6)_2$ or tetrazole;

$R_9$ is $(CH_2)_n$, $C_{1-10}$alkyl, $C_{2-10}$alkenyl or phenyl all of which may be unsubustitued or substituted by one or more OH, $N(R_6)_2$, COOH, halogen, >C=O or $XC_{1-5}$alkyl;

X is $(CH_2)_n$, O, $NR_6$ or $S(O)_p$;

Y is $CH_3$, —$X(CH_2)_nAr$ or Ar;

$R_{10}$ is hydrogen, phenyl, benzyl, radical (b) from above, imidazolyl, thienyl, furyl, pyrazolyl, isoxazolyl, pyridyl or tetrazolyl all of which may be unsubustituted or substituted by $C_{1-6}$alkyl, $C_{1-6}$alkoxy, Cl, Br, F, I, $N(R_{11})_2$, —$CO_2R_7$, —$SO_{2l NHR7}$, —$SO_3R_7$, —$CON(R_{7l})_2$, OH, $NO_2$, —$S(O)_pC_{1-6}$alkyl, or —$NR_7COC_{1-6}$alkyl;

$R_{11}$ is Ar, $C_{3-8}$cycloalkyl, $C_{1-8}$alkyl, $C_{2-8}$alkenyl, $C_{2-8}$alkynyl all of which may be unsubustituted or subsituted by one or more OH, $CH_2OH$, $N(R_6)_2$ or halogen;

Ar is:

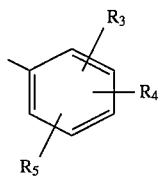
(a)

or

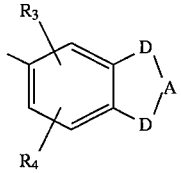
(b)

naphthyl, indolyl, pyridyl, thienyl, oxazolidinyl, oxazolyl, thiazolyl, benzoyl, isothiazolyl, pyrazolyl, triazolyl, tetrazolyl, imidazolyl, imidazolidinyl, furyl, thiazolidinyl, isoxazolyl, oxadiazolyl, thiadiazolyl, morpholinyl, piperidinyl, piperazinyl, pyrrolyl, or pyrimidyl; all of which may be unsubustituted or substituted by one or more $R_3$ or $R_4$ groups;

A is C=O, or $[C(R_6)_2]_m$;

[B] D is —$CH_2$— or —O—;

n is 0 to 6;

m is 1 or 2;

p is 0, 1 or 2;

and the dotted line indicates the optional presence of a double bond; or a pharmaceutically acceptable salt thereof, provided $R_{10}$ is not H when $R_1$, $R_2$ and $R_{11}$ are all unsubstituted phenyl and $R_8$ is COOH, and X is $(CH_2)_n$ when n= 0 and $R_8$ is COOH and provided the compound of Formula I is not 1-[2-( 4-chlorophenyl)-3-(2,4-dichlorophenyl)-1-(4-methoxyphenyl)propyl]-1H-imidazole, and provided that $R_3$, $R_4$, and $R_5$ are not hydrogen.

2. A compound of claim 1 wherein $R_1$ is (b); $R_8$ is COOH; $R_{10}$ is H; $R_{11}$ is imidazolyl or phenyl; p is 1; $R_2$ is (a); $R_3$, $R_4$, and $R_5$ are independently meO; —$O(CH_2)_mP_8$ or XAr optionally substituted with COOH and $R_2$ is substituted in the ortho position.

3. A compound of claim 1 selected from the group consisting of:

(2E)-3-(2-n-Butyl-1H-imidazol-4(5)-yl)-3-( 2,4-dimethoxyphenyl)-2-(3,4-methylenedioxybenzyl)prop-2-enoic acid;

(2R,S)-3,3-Bis-(4-methoxyphenyl)-2-(3,4-methylenedioxybenzyl)propionic acid;

3,3-Diphenyl-2-(3,4-methylenedioxybenzyl)prop- 2-enoic acid;

3,3-Bis-(4-methoxyphenyl)-2-( 3,4-methylenedioxybenzyl)prop-2-enoic acid;

3,3-Bis-(3,4-methylenedioxyphenyl)-2-( 3,4-methylenedioxybenzyl)prop-2-enoic acid;

(2E)-3-(2-n-Butyl-1-methyl-1H-imidazol-5-yl)-3-( 2-carboxymethoxy-4-methoxyphenyl)-2-(3,4-methylenedioxybenzyl)prop-2-enoic acid;

(2E)-3(2-n-Butyl-1-trimethylsilylethyloxymethoxy-1H-imidazol- 5-yl)-3-(2-carboxymethoxy-4-methoxyphenyl)-2-(3,4-methylenedioxybenzyl)prop- 2-enoic acid;

(2Z)-Methyl-3-(2-Carboxymethoxy-4-methoxyphenyl)-3-phenyl- 2-(3,4-methylenedioxybenzyl)prop-2-enoate;

(2Z)-3-(2-Carboxymethoxy-4-methoxyphenyl)-3-phenyl-2-( 3,4-methylenedioxybenzyl)prop-2-enoic acid;

2E)-3-(2-Carboxymethoxy-4-methoxyphenyl)-3-phenyl-2-( 3,4-methylenedioxybenzyl)prop-2-enoic acid; and (2E)-3-(2-n-Butyl-1-methyl-1H-imidazol-5-yl)-3-(2,4-dimethoxyphenyl)-2-(3,4-methylenedioxybenzyl)prop-2-enoic acid.

4. A pharmaceutical composition comprising a compound of claim 1 and a pharmaceutically acceptable carrier.

5. A method of antagonizing endothelin receptors which comprises administering to a subject in need thereof, an effective amount to antagonize endothelin receptors of a compound of claim 1.

6. A method of treating hypertension which comprises administering to a subject in need thereof, an effective mount of a compound of claim 1.

7. A method of treating renal failure which comprises administering to a subject in need thereof, an effective mount of a compound of claim 1.

8. A method of treating cerebrovascular disease which comprises administering to a subject in need thereof, an effective amount of a compound of claim 1.

* * * * *